United States Patent
Burke et al.

(10) Patent No.: US 7,402,178 B2
(45) Date of Patent: Jul. 22, 2008

(54) GARMENT PROCESSING WITH BIOLOGICAL SANITIZATION AND INSPECTION PROCEDURES

(75) Inventors: Joseph P. Burke, Edina, MN (US); Julie L. Stockhaus, Chaska, MN (US); Charles R. Knott, Chandler, AZ (US); Deborah A. Pikovsky, Excelsior, MN (US)

(73) Assignee: G & K Services, Inc., Minnetonka, MN (US)

( * ) Notice: Subject to any disclaimer, the term of this patent is extended or adjusted under 35 U.S.C. 154(b) by 61 days.

(21) Appl. No.: 11/317,625

(22) Filed: Dec. 22, 2005

(65) Prior Publication Data

US 2006/0170913 A1 Aug. 3, 2006

Related U.S. Application Data

(60) Provisional application No. 60/639,106, filed on Dec. 23, 2004.

(51) Int. Cl.
*C11D 3/00* (2006.01)
(52) U.S. Cl. .............................. 8/137; 435/30; 700/225
(58) Field of Classification Search ................... 8/137, 8/142, 401; 510/280, 320, 322, 437
See application file for complete search history.

(56) References Cited

U.S. PATENT DOCUMENTS

| | | | |
|---|---|---|---|
| 2,889,799 A | 6/1959 | Korpman |
| 3,850,367 A | 11/1974 | Fortriede |
| 4,873,878 A | 10/1989 | Milton |
| 4,998,620 A | 3/1991 | Taylor |

(Continued)

FOREIGN PATENT DOCUMENTS

DE  26 59 765  7/1978

(Continued)

OTHER PUBLICATIONS

PCT International Search Report dated May 12, 2006.

(Continued)

*Primary Examiner*—Mark Eashoo
*Assistant Examiner*—Thuy-Ai N Nguyen
(74) *Attorney, Agent, or Firm*—Brooks, Cameron & Huebsch, PLLC (57) ABSTRACT

Biological inspection procedures and surface sanitization procedures are incorporated with a garment providing service to look for and monitor the presence of microbes, such as bacteria in particular, and to eliminate such microbes within the garment service. Biological inspection procedures can be conducted on the garments themselves, or any surface of the garment facility, such as a surface onto which the garments may come into contact after laundering. Preferably, a washing procedure is conducted based upon a cleaning formulation to also minimize the presence of microbes. Garments are preferably inspected after they are laundered and ready for delivery to the customer. Facility surfaces, such as sorting and/or folding tables that may be utilized after laundering, are sanitized and then may be tested in accordance with the present invention to minimize the potential for contamination of garments from such surfaces. Optionally, the equipment that is used after laundering for such activities can be dedicated for processing garments in accordance with the biological inspection service as such garments are to be delivered to a customer, such as a processor within the food industry.

21 Claims, 3 Drawing Sheets

U.S. PATENT DOCUMENTS

| | | | |
|---|---|---|---|
| 5,046,844 A | 9/1991 | Milton | |
| 5,652,966 A | 8/1997 | Reinert, Sr. | |
| D393,601 S | 4/1998 | Skiffington | |
| 5,780,098 A | 7/1998 | Battles | |
| 5,917,592 A | 6/1999 | Skiffington | |
| 6,055,050 A | 4/2000 | Skiffington | |
| 6,136,204 A | 10/2000 | Krejci | |
| 6,887,681 B2 * | 5/2005 | DiCesare et al. | 435/30 |
| 2003/0019798 A1 | 1/2003 | Capps et al. | |
| 2003/0074105 A1 * | 4/2003 | Capps et al. | 700/225 |
| 2003/0129765 A1 | 7/2003 | DiCesare et al. | |

FOREIGN PATENT DOCUMENTS

| | | |
|---|---|---|
| DE | 37 18 553 | 12/1987 |
| EP | 0 185 970 | 12/1985 |

OTHER PUBLICATIONS

3M Petrifilm™ Plate Reader, *Consistent, automated reading and recording of results of 3M™ Petrifilm™ Plates in 4 seconds*, brochure, 3M Microbiology, 2004.

3M Microbiology, *Methods of Testing Available Using 3M Microbiology products*, brochure, 3M 2002.

3M Quick Swab, *The easy, all-in-one swab for consistent surface sampling*. Brochure, 3M Microbiology, 2004.

3M™ Petrifilm™ Plates, Product Listing, 3M Microbiology, Jun. 1, 2004.

3M Petrifilm™ Plates, *Environmental Monitoring Procedures*, brochure, 3M Microbiology, 2003.

3M™ Petrifilm™ Plates, *Sample Preparation*, brochure, 3M Microbiology, 2003.

3M Petrifilm™ Plate, *Guide to Dilution Preparation*, brochure, 3M Microbiology, 2003.

3M Laboratory Start-up Package, *An affordable way to perform on-site micro testing* .brochure, 3M, 2000.

3M Quick Swab, *Reminders for Use* brochure, 3M, 2003.

UniFirst Helping Customers Meet HACCP Standards, 2 page brochure, UniFirst.

3M Microbiology, *Starting or Expanding Your Environmental Monitoring Program*, brochure, 3M Microbiology, Fall 2002.

\* cited by examiner

GARMENT PROCESSING WITH BIOLOGICAL SANITIZATION AND INSPECTION PROCEDURES

REFERENCE TO RELATED APPLICATIONS

This application claims the benefit of U.S. Provisional application Ser. No. 60/639,106, filed Dec. 23, 2004, entitled, "GARMENT PROCESSING WITH BIOLOGICAL INSPECTION PROCEDURES," which application is incorporated herein by reference in its entirety.

TECHNICAL FIELD

The present invention is directed to methods of cleaning, sanitizing and disinfecting processing surfaces and garments within a service of providing garments for use in particular industries and other services. In particular, the present invention is directed to methods of cleaning, sanitizing and disinfecting processing surfaces and garments having particular use in certain industries, such as food processing, including biological contaminant inspection and monitoring.

BACKGROUND OF THE INVENTION

Garments are provided for many different service providers and industrial applications where workers are given garments, such as uniforms, protective clothing, or the like, for purposes of personal safety, product safety, cleanliness and many other practical reasons. A service industry exists for delivering clean garments to facilities in many such other industries and services and for subsequently picking up soiled or used garments, replacing them with clean garments, and laundering the soiled garments as part of a cycle. Customers of such a garment service typically purchase or lease a sufficient quantity of clothing articles so that they will have clean garments ready on a daily or other periodic basis to its employees, which quantity takes into account the full processing cycle. As such, the garment service can be laundering one or more garments per employee while each employee is adequately provided with a supply of garments ready for wearing based upon the frequency of the delivery cycle. Typical garments that are provided from such garment services include shirts, pants, smocks, frocks, coats, suits, coveralls, aprons, gloves, headwear and footwear.

The laundering or washing and drying steps of such a garment supply service is normally a selective process based upon the garment to be cleaned. Such selection may include a sorting of the garments to be laundered in different ways based upon factors including colors, durability, and the classification of the dirt or stains on the garments. The selection also applies to wash parameters of any such laundering step, of which, a service may have a number of different wash processes that may be selectively conducted on a selected classification of garments. Basic parameters of a typical selective wash process or cleaning formulation include water temperature, wash time, chemistry and mechanical action. By chemistry, it is meant the use of desired quantities of detergents and other cleaning additives like bleach and alkalinity adjusters. Other chemical solvents or other additives are sometimes added based upon a specific cleaning formulation as desired for a particular stain removal process. Wash time controls include not only the wash time, but also the timing aspects of the chemical delivery and the mechanical action. Moreover, many different types of washing equipment are commercially available with many different mechanical agitation and wash cycles and manners of movement of the garments within the washers during the wash process. In these commercial washing machines, the chemicals that are used as the detergents, bleach, and other additives are typically injected into a temperature controlled water supply to be active within the washing compartment of the washing machine based upon a selected cleaning control process.

The laundering step for a selective class of garments is normally controlled to include the cleaning formulation with the wash timing aspects such as wash and rinse periods and the number and duration thereof. Likewise, the drying of the garments may be controlled for selective drying temperatures and time aspects.

A class of garments is often importantly characterized by the industry within which the garments are used. As examples, coveralls usable within the semiconductor processing industry must be cleaned to remove possible particulate contaminants, clothing worn within the automotive repair industry must be cleaned of particular oils, silicone and grease, and clothing worn in certain food processing industries, such as meat processing or dairy production, require the removal of organic matter like blood and dairy stains. As such, a basic wash process is typically modified based upon such a classification to develop a cleaning formulation that will remove the required matter and/or stains by adjusting the chemical detergents, alkalinity, bleach, water temperature, and wash/rinse cycle timing and duration aspects. Moreover, it is known to control one cleaning formulation from another within a washing machine by utilizing a microprocessor having multiple formulations stored within memory and from which a desired formulation control process can be selected.

The food industry is a specialty industry like many others that raises distinct considerations for laundering. Food processing is distinct from most in that food stains or food matter and moisture on a garment can provide the basis for growth of microbes, in particular bacteria, that can be considered contaminants in food processing and potentially cause food safety issues. Thus, cleaning formulations have been developed in particular for the purpose of reducing microbes, and in particular certain bacteria, on garments after laundering and for delivery to customers within the food service industry. The use of organic-killing laundering chemicals, like bleach, wash solution alkalinity, and higher temperature water are known for killing certain bacteria. The food service industry includes food processors like meat, dairy, baked goods and other prepared food producers, food packers and packagers, food preparers like bakers and cooks in production facilities as well as in food service caterers and restaurants, food retailers, wholesalers and service providers, including grocery stores and the like.

A typical prior art process for a garment service starts with the delivery of clean garments to a customer and pick up of soiled garments and further includes the steps of transporting the soiled garments back to a processing facility, sorting the garments, washing the garments in accordance with a chosen cleaning formulation, inspecting the garments for need of repair or replacement, and preparing the garments for clean shipment to the customer. For a specific industry, such as food service, the sorting and cleaning formulation wash steps can be specific to that industry, as described above. The step of preparing the garments for the customer is usually based upon customer specifications as to how the garments are to be delivered. Transportation of the garments from the customer to the processing facility is typically done by putting the soiled garments into large bags or slings, or bins, which are then loaded onto trucks. Once the garments arrive at the processing facility, the slings are emptied and the soiled garments are sorted according to a desired classification based upon the way they are intended to be washed. Sorted garments are then typically reloaded into separate slings. Inspection for repair or replacement of garments normally is done after the washing and drying process. Repaired or replacement garments may be subsequently put back into the service cycle for washing and drying. In preparing garments for delivery to the customer, many different post-wash steps are known to be conducted for the purpose of providing the garments to the customer in a desired way. As an example, for wrinkle removal, steam tunnels have been developed so that garments can be hung on hangers and conveyed as they are hung through the steam tunnel. Or, garments may be individually pressed using pressing equipment. The garments may be further folded and packaged or kept on hangers for delivery to the customer. Transportation containers are also known within which the garments can be stored for delivery of the clean garments to the customer.

SUMMARY OF THE INVENTION

The present invention overcomes shortcomings of the prior art by providing processes for minimizing the potential for contamination of a customer's service or production facility from microbial contamination by garments that have been laundered. In particular, the present invention is advantageous for providing garments, such as for use within the food processing industry, to minimize potential microbial contamination from garments provided to customers, such as food processors, prepared food producers, food packers and packagers, food preparers, food sellers, and any other food handler.

In accordance with the present invention, biological controls including sanitization procedures and biological inspection procedures are incorporated with a garment providing service to reduce or eliminate, and identify and monitor the presence of microbes, such as bacteria in particular, within the garment service. Sanitization procedures can be performed on one or more surfaces of a garment facility, such as a laundering facility for garments, that is/are likely to come into contact with garments before, during, or, in particular, after laundering. Biological inspection procedures can be conducted on the garments themselves, and/or on any surface of the garment facility, such as a surface onto which the garments may come into contact after washing. Preferably, a processing surface is sanitized followed by such a biological inspection as a matter of showing compliance with garment sanitizing standards depending on industry standards and/or customer specifications. Also, a washing procedure is conducted based upon a cleaning formulation to also minimize the presence of microbes. Garments are preferably inspected after they are laundered and ready for delivery to the customer. Facility surfaces, such as sorting and/or folding tables that may be utilized, in particular, after laundering, may be tested in accordance with the present invention to verify compliance with sanitization procedures or customer and/or internal operational standards and to minimize the potential for contamination of garments from such surfaces. Wash process personnel are preferably also clothed in sanitized uniforms and gloves for handling garments after laundering. Optionally, the equipment that is used after laundering for such activities may be controlled to be only used for processing garments in accordance with the biological inspection service as such garments are to be delivered to a customer, such as a processor within the food industry.

In accordance with one aspect of the present invention, a method of processing garments as used by a customer within a service field by a garment service provider at a garment service facility includes obtaining soiled garments from the customer, laundering the soiled garments by the steps of washing the garments and drying the garments, preparing the garments for delivery back to the customer; and sanitizing a processing surface within the garment service facility, wherein the processing surface comprises a surface that is used in processing the garments after laundering. The method of processing garments more preferably also includes a step of conducting a facility biological inspection procedure the processing surface within the garment service facility after it is sanitized, wherein the biological inspection procedure comprises obtaining a biological sample from the surface used in processing garments and testing the sample for the presence of microbes. Preferably, the facility biological inspection procedure is conducted on a surface of an inspection station after the laundering step and prior to any garments being processed thereon. More preferably, the facility biological inspection procedure includes an ATP test.

In accordance with another aspect of the present invention, a method of processing garments as used by a customer within a service field by a garment service provider at a garment service facility includes obtaining soiled garments from the customer, laundering the soiled garments by the steps of washing the garments and drying the garments, preparing the garments for delivery back to the customer, and conducting a garment biological inspection procedure on at least one garment while within the garment service facility by obtaining a biological sample from the garment and testing the sample for the presence of microbes. The biological inspection procedure can be conducted on one garment as a representative sample from any group of any size of garments, or any number including all garments can be tested. Preferably, the garment biological inspection procedure includes a CFU test. Also, the method is preferably to include a sanitization step of a processing surface within the garment service facility, the processing surface comprising a surface that is used in the processing of the garments after laundering. More preferably, a facility biological inspection procedure is also conducted on the processing surface within the garment service facility, wherein the biological inspection procedure comprises obtaining a biological sample from the surface used in processing garments and testing the sample for the presence of microbes. Then, results from the garment biological inspection procedure can be reviewed against and correlated with results of the facility biological inspection procedure to demonstrate satisfactory facility biological inspection procedure results. Such inspection results can then also be reported to the customer to show biological inspection compliance.

In yet another aspect of the present invention, a method of processing garments as used by a customer within a service field by a garment service provider at a garment service facility by obtaining soiled garments from the customer, laundering the soiled garments by the steps of washing the garments and drying the garments, performing a biological inspection on at least one of a facility surface and a garment, preparing the garments for delivery back to the customer, and controlling the handling of the garments between the garment service facility and the customer by transporting the garments within a container, wherein the container is provided with an indication that the garments are specified for a specific garment process that includes a biological inspection. Preferably, a container can comprise a sling, wherein the sling can include a color-coding, specific indicia, marking, and/or a closure with a tamper evident feature. More preferably, this method is conducted with both a facility biological inspection procedure, such as set out above, and a garment biological inspection procedure, such as also set out above.

DETAILED DESCRIPTION OF THE INVENTION

Figure 1:
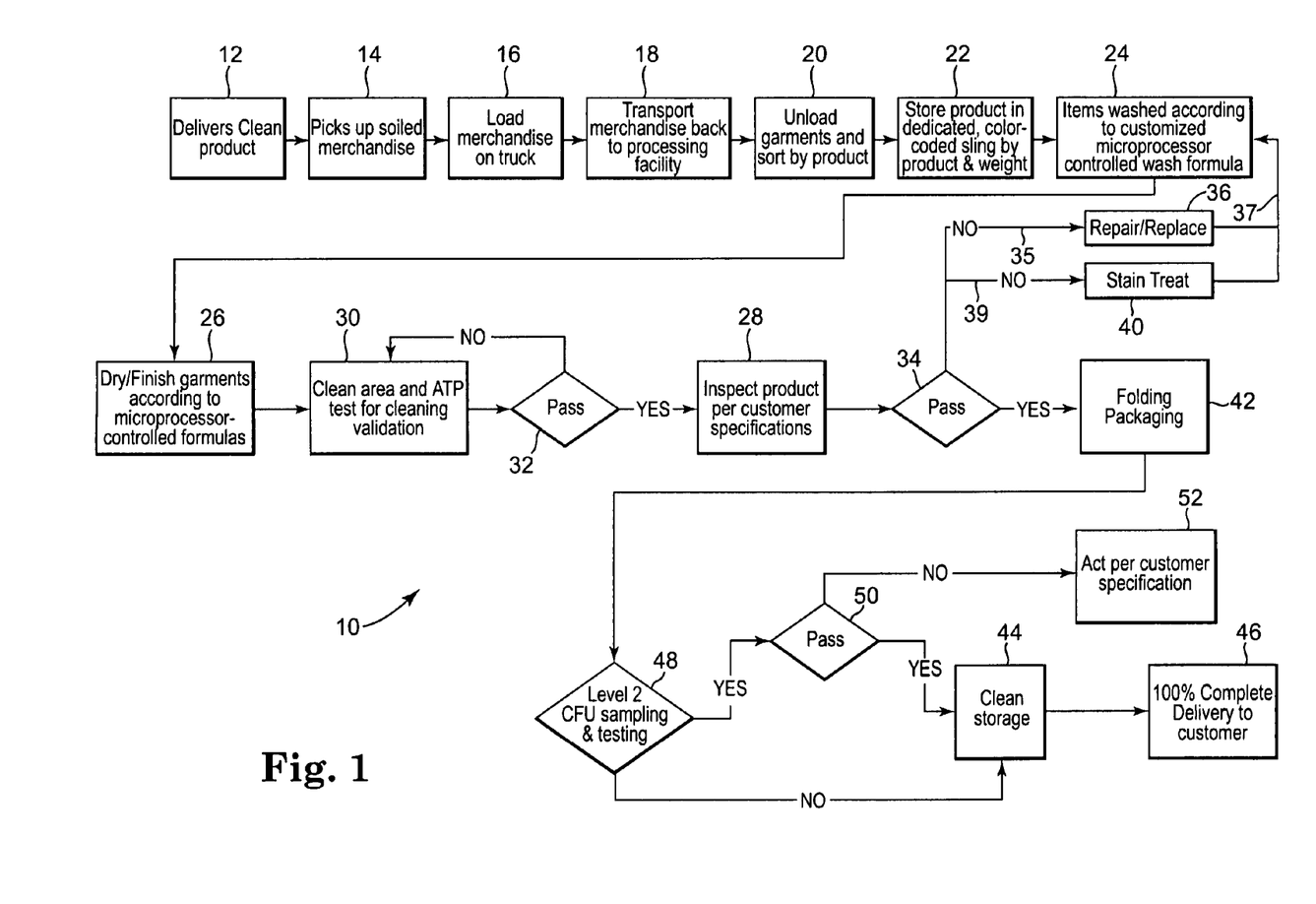
FIG. 1 is a schematic diagram of a garment services process for use within a service field that includes biological inspection procedures as part of a process in accordance with the present invention for minimizing the risk of contamination of a customer's service or production facility from microbe contamination by way of garments processed by a garment services provider.

With reference to the drawings, wherein like components are labeled with like numerals throughout the several figures, and initially to FIG. 1, a garment services process is schematically illustrated that includes many garment processing steps from the delivery of clean product and pick up of soiled garments up to the delivery of new clean garments, and includes in particular the provision of sanitizing or cleaning steps along with biological inspection processes at a plurality of points within a process cycle for minimizing the presence of microbes, and in particular bacteria, on garments after the process is completed. It is understood that only one or more than two such sanitizing and biological inspection processes can be incorporated within a process cycle based upon specific requirements of a customer or to ensure the minimizing of microbe presence on processed garments. As used throughout this application, a garment services process includes any and all steps that may be conducted from pick of garments through the delivery of clean garments such as the steps related to laundering the garments, but also the transporting, packaging, and handling of garments. Also, as discussed above in the Background section of the subject application, a process in accordance with the present invention finds particular applicability within the food processing or services industry in that the presence of certain types of microbes, in particular bacteria, may be considered a contaminate for garments usable in the food industry. However, it is also understood that a process in accordance with the present invention for providing at least one biological inspection procedure may be applicable to any particular industry or services where there may be a desire to minimize the presence of microbes on garments. Furthermore, for a particular application, it may be only desirable to ensure that microbes of any specific type are merely limited below a certain threshold value. That is to say, the biological inspection procedure may be used to ensure less than a threshold value of microbe presence on garments without necessarily minimizing such.

Moreover, and as discussed in greater detail below, it is contemplated to provide a biological inspection process for microbes to at least one of a garment after it is the laundered. Any number or all of garments can be inspected pursuant to the biological inspection process, but it is preferable to inspect only a representative sample of the total lot at a sufficient frequency to satisfy compliance with a desired level of garment sanitization or cleanliness with respect to any one or more microbe(s). Such a level of compliance can be based upon any predetermined standards, such as provided industry wide, or customer specific, or based upon other criteria determined by the garment services provider and/or any customer. It is also contemplated to sanitize one or more of the surfaces of a processing facility that may contact garments after they are laundered and before they are ready for transport back to a customer. To show compliance with desired sanitization levels and to ensure sufficiently sanitized garments, it is also contemplated to conduct a biological inspection process on one or more of the processing surfaces that contact laundered garments after they are sanitized. If sanitary conditions exist for whatever reasons without a specific surface sanitization step, such a facility or surface biological inspection process step can be conducted without first performing a specific sanitization procedure. Preferably, both garments and a processing surface are biologically inspected to show compliance with a desired microbe presence level. The term microbe is meant to include any microscopic and ultramicroscopic organisms, such as spirochetes, bacteria, rickettsiae, viruses, and the like. The presence of such microbes is monitored and thus may be desirably maintained below a selected threshold value for any particular industrial or services application. Any type of microbe test procedure is contemplated as a suitable biological inspection process as chosen for any service field or industry.

For purposes of explanation of the present invention, and as particularly applicable to the food service field, microbes of concern comprise, in particular, bacteria. Moreover the specific bacteria that may be of concern for a particular food industry can be any of known bacteria that may be determined to be monitored for a particular application. Preferably, the biological inspection procedure looks for the presence of most any microbial organism so that it is unnecessary to provide selected tests on an organism specific basis. A colony forming unit (CFU) test, for example, detects any aerobic microbe as may be present on a detection plate and as may be inspected by a plate reader.

FIG. 1 shows a complete cycle of a garment services process throughout which a quality assurance process is incorporated based upon the inclusion of at least one biological inspection procedure and/or at least one facility sanitization procedure. Moreover, FIG. 1 shows one specific garment services process in accordance with the present invention, which process can be modified in accordance with customer specifications as may be desirable or required for a particular application. The specific standard operating procedures, many examples of which are illustrated in FIG. 1, for any particular application can likewise be modified to define the specific processes and protocols that ensure compliance of the process outcomes to the customer requirements. Also, the inclusion of at least one biological inspection procedure and/or sanitization procedure demonstrates control aspects for process control repeatability by the garment services provider as well as demonstrating to the garment services provider and its customers the consistency and efficiency of a particular process, such as including laundering, sorting and preparation steps.

Referring to FIG. 1, a garment services process 10 is schematically illustrated starting from the delivery of clean garments to a customer within a service field as indicated at box 12. Box 14 indicates the picking up of soiled garments from the customer followed by the loading of the soiled garments within a transportation vehicle, such as truck, illustrated at box 16. The garments that are delivered and as picked up as soiled garments can be any specific garment, product or combination of garment types and products as may be applicable to the service field of the customer. The garments may be provided in containers of any particular variety or may be loosely loaded for transportation as desired. However, it is preferable that for garments to be processed in accordance with the present invention, that such garments be contained in an approved container as may be determined between the customer and garment services provider to ensure the proper handling and processing of the garments.

Such a containment device or system may include features for identification purposes and/or for isolation purposes. For example, the container may be color-coded or provided with the specific markings, indicia, tags or the like to identify the garments therein as being designated for a process including biological inspection in accordance with the present invention. Or, a different size, shape, type or configuration for a container can be utilized for such purpose. Moreover, such a container may be open or closed, but preferably a container for use in accordance with the present invention is closeable to maintain the garments isolated from others at the customers facility, in transport, and into the garment processing facility for clear identification to the garment services provider. Containers are also preferably easily sanitizable so that the containers do not add to the provision of any microbes to the garments transported therein.

Figure 2:
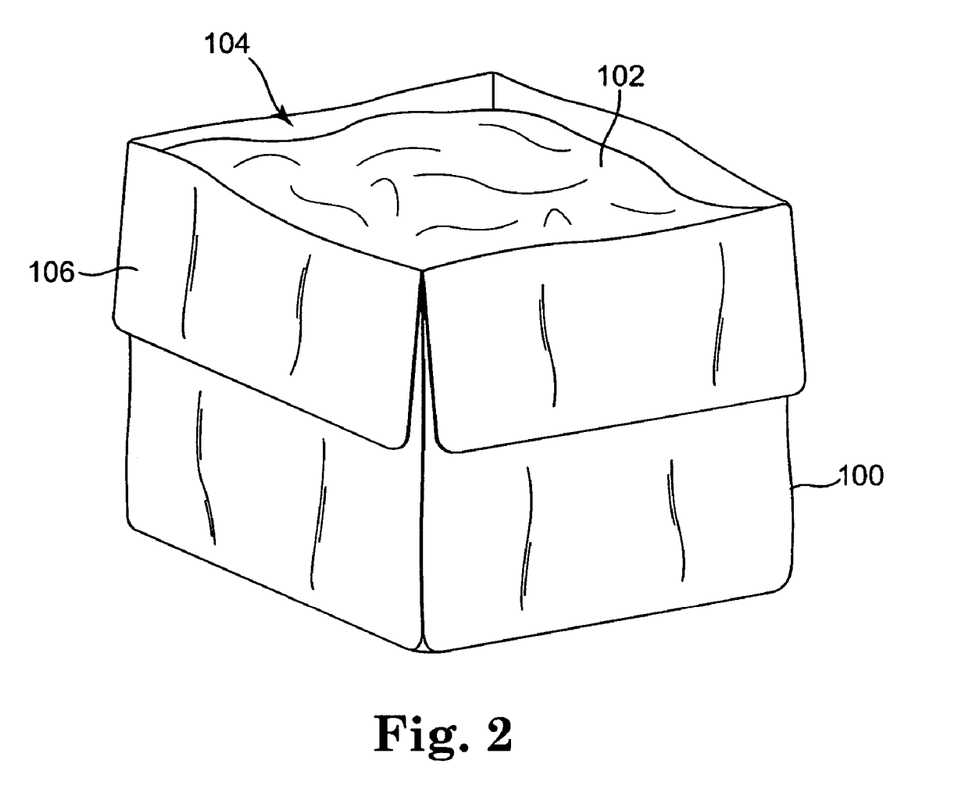
FIG. 2 is an illustration of a sling type container that is usable in transporting soiled garments from a customer's facility to a garment service provider's facility for processing, the sling container is illustrated in perspective with the top open and with soiled garments packed therein.
Figure 3:
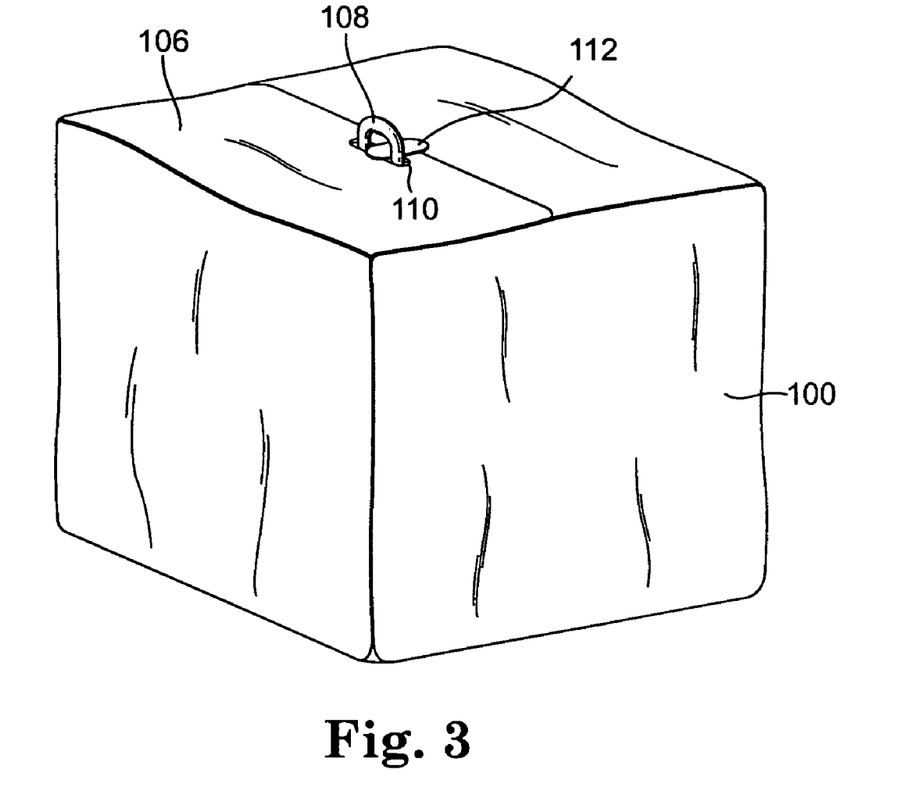
FIG. 3 is an illustration of the sling type container of FIG. 2 but with the top of the sling closed and further showing a tamper evident tag provided on the sling closure.

A preferred type of container for packing with soiled garments and that is easily transportable to the garment processing facility and transportable within a garment processing facility for handling purposes is illustrated in FIGS. 2 and 3. The illustrated container preferably comprises a garment sling 100 that is comprised of flexible material and that is capable of creating a sufficient internal volume for receiving a quantity of garments 102 and that is further capable of being opened and closed. Such garment slings 100 are themselves well-known as used within garment processing facilities and are typically made up from flexible polyester material to define and internal volume that is preferably related to the amount of clothing that is expected to be washed within a particular washing machine of a particular capacity, normally based on weight. The garments may be sorted, staged and repacked in such slings prior to laundering. As also shown in FIG. 2, the sling 100 preferably includes a closure feature 104, which preferably comprises a plurality of flaps 106 that are folded over the open top of the sling 100 after the garments 102 are packed therein as such flat type closures are well-known. Such a sling 100 can be closed as illustrated in FIG. 3 by folding a first opposed set of flaps over the open top and then folding a second opposed set of flaps over the first opposed set of flaps. Such a closure can be secured in place as conventionally known by providing a ring or other fastener element 108 connected with an outside facing surface of one flap that passes through a grommet 110 or other opening of an opposed flap. The flaps can be maintained in the closed position by any conventional additional fastener and/or locking feature that prevents the fastener element 108 from passing back through the grommet 110. Other closure mechanisms and as known or developed are contemplated and can be easily substituted for the example illustrated in FIGS. 2 and 3. Known garment slings 100 are openable and closeable also at the bottom, which bottom is preferably also closeable in a secure manner to prevent garments 102 from falling out of the sling 100 during transportation and handling. Any other container that is flexible or rigid and that is open or that is closeable is also contemplated including any number of other features for transportation and handling purposes. Flexible garment slings of washable material are preferred in that they are easily maintained and sanitized, such as by a laundering process.

One preferred aspect of the present invention is the optional incorporation of a tamper evident feature as applied to the closure of a container, such as the garment sling 100. Many different types of tamper evident tags, tapes, rings, wires and other devices that can be attached to a closure feature, such as the faster element 108, have been developed. Preferably, such a tamper evident device would be of a type that must be broken or otherwise destroyed if the closure of a container is opened. More preferably, such a tamper evident device is inexpensive and easily removed to facilitate garment services provider opening. As such, inexpensive tamper evident tags, tapes, rings, wires and the like that are easy to remove are preferred, as such are well-known as provided for other types of container closures. Preferably also, such a tamper evident tag would include an identification feature, such as to identify the customer, as may be provided by color coding, indicia, tags with numbers or other indicia, other markings, or the like.

Once one or more containers, such as garment slings 100, are loaded within a transport vehicle, such as a delivery truck, the garments can be transported and delivered to the garment services provider facility, which step is illustrated in FIG. 1 by box 18. It is contemplated that for a more restrictive compliance process as may be desired by a customer, a dedicated vehicle can be utilized for this purpose. Such a dedicated vehicle can be customer specific or restricted on the service field of the garments, such as for food services, or may comprise only a portion of a vehicle as such may be partitioned or otherwise sectioned from the vehicle area that is utilized for other garments on a customer basis or service field basis. Slings 100 that are to be identified on a customer basis, service field basis, or other basis can include tags, colors, indicia, or other markings for such identification purpose, which as above, may be incorporated within a tamper evident feature. It is also contemplated that the vehicle storage area can be secured by tamper evident features in a similar manner as that discussed above with respect to the garment containers. The transportation step, labeled as box 18 in FIG. 1, may instead comprise merely loading the garments in the vehicle in any containers or without any specific container.

FIG. 1 next shows the preferable steps of unloading and sorting the garments, noted as box 20, and of staging the garments, noted as box 22, before laundering. Once the garments are unloaded or removed from any container, such as sling 100, the garments are preferably sorted according to the type of garment. For example, where shirts and pants are collectively transported within a sling 100, they may be separated at step 20. However, the garments may not be sorted at all. The staging step 22 preferably comprises procedures for gathering a proper quantity by weight of sorted garments in preparation for washing in accordance with the capacity of a washing machine to be used. That is, the sorted garments are separated into lots for washing. Such garments may or may not be combined with other garments (potentially from other customers) in preparing lots suitable for a washing machine's capacity. Preferably, the lots are weighed to meet load limitations of the washing machine. Also at this stage, any garments requiring special handling or washing can be separated from the other garments. For example, a garment may be identified as needing a special wash treatment to remove a particular stain not normally expected from the industry or service of that particular customer, in which case, it may require special handling, washing and tracking. In accordance with an aspect of the present invention to ensure proper processing to a particular customer, in particular where biological inspection is to be conducted, it may be preferable to keep different customers garments separated from one another during the staging and washing steps to reduce the risk of cross contamination.

Laundering of the garments is conducted within washing step 24 and drying step 26 has shown in FIG. 1, each of which process is preferably microprocessor controlled. As discussed above, a cleaning formulation is preferably controlled by such microprocessor by injecting relevant chemicals and additives at appropriate stages of the wash cycle, which wash rinse and mechanical agitation aspects are also preferably controlled. Such cleaning formulation also includes the time and temperature aspects of the wash water and chemicals as well as the timing of the wash cycles including agitation aspects and the like. In accordance with the present invention to minimize or reduce the presence of microbes on the garments below a threshold value, the cleaning formulation should be selected for that purpose. Many different cleaning formulations are known and have been developed for the purpose of reducing specific microbes, like bacteria, during the laundering process. As noted above, such cleaning formulations include the use and timing of controlled water temperature, detergents, bleaches, pH (alkalinity) control and/or the use of other additives. The specific formulation of washing the garments for the purpose of reducing any one or more class of microbes is not an important aspect of the present invention, whereas many commercially available detergents, additives and other formulation factors are well-known for such purpose with the understanding that such formulations change from time to time as commercially available chemicals are developed. However, where the biological inspection procedures described in detail below might determine the presence of microbe contaminants above an acceptable level on finished garments, it is contemplated to use that information as feedback for the purpose of modifying the cleaning formulation to more effectively remove or kill such microbe.

As such, step 24 represents the application of a selected specific controlled cleaning formulation to a classification of garments to be effectively laundered consistent with the expectations of the customer. In the case of the food industry, the removal or killing of specified bacteria may be most important. The washing step 24 may also include sub-steps of pre-washing for stain removal as such stains may be of a type expected from that customer based upon its industry or service or otherwise. Also, it is understood that a cleaning formulation may be further specified according to the type of stain that may be encountered based upon a specific subset of stain making materials. For example, in meat processing, a different cleaning formulation may be applied based on the type of meat process, such as differently between beef, pork, lamb, poultry, fish, or the like, or based on the exposure of the worker to other soiling materials like food dyes, or the like. Such wash formulas preferably comprise at least a detergent (preferably a non-phosphorous detergent), an alkalinity agent, and oxidizers and utilize softened water at a temperature between 145 degrees and 180 degrees Fahrenheit. Preferably also, active bleach is also utilized at an effective amount, and the wash solution pH is controlled to be twelve or greater. To effectively prevent significant microbial contaminants from the wash process, the garments themselves (after removal from the wash) preferably leave the washing machine having a pH of between 6.5 and 7.2.

Step 26 represents the drying of the garments as transported from the washing machine to a dryer and as dried sufficiently for further garment processing. Like the washing process, the garments are preferably dried in accordance with the garment type as they have been sorted and staged and may be dedicated for the specific process with biological inspection or otherwise mixed if appropriate. Such drying step is generally conducted in accordance with recommendations of the garment manufacturer for the specific garment in question and taking into account any desired finishing steps.

A next garment processing step is illustrated at box 28 that is shown after a facility sanitization and biological inspection step 30 and a related decision step 32 that will be discussed in greater detail below. Step 28 preferably comprises a garment inspection step for the purpose of checking for any needed repairs, stains or garments that need replacement. In particular, the garment inspection step 28 preferably includes an inspection of each garment per acceptability standards as may be determined by the garment processing service or as agreed with the customer. Preferably, each garment is inspected for repairs that may be necessary to the garment. A decision step is illustrated at 34, and if a repair is needed to a garment, that garment is preferably removed from its lot and sent to a repair/replacement station 36 as indicated by line 35. The garment would then be repaired according to developed standards. Examples of garment repair failures include garments showing significant signs of damage, missing or broken buttons or snaps, damaged zippers, rips or tears, or holes. Likewise, if it is determined that a garment is so damaged to be in need of replacement, that garment would be sent to the repair/replacement station 36 for replacement. Subsequent to a decision to repair or replace a garment at station 36, the repaired or replacement garment is preferably then resubmitted into the wash step 24 as indicated by line 37. Also as part of the inspection step 28, each garment is checked for stains that may still exist after being laundered and in accordance with standards set by the garment processor and/or with the customer. Each garment is also preferably checked for any foreign object contamination that may be provided in pockets or the like. If it is determined in step 34 that a stain is unacceptable, the garment is sent as indicated via line 39 to a stain treatment station 40. There, any garment that exhibits such a stain can be stain treated by any conventional stain removal procedure and subsequently resubmitted to the wash step 24 as also indicated by line 37. If a foreign object contaminant is found, it is preferable at decision step 34 to also reject the garment for resubmission to the wash step 24.

Garments that pass the inspection process are then preferably forwarded to a preparation station 42 wherein each garment is prepared to be sent to the customer in accordance with agreed-upon specifications. In some cases, the garments may merely be packaged or packed within containers, which containers are preferably sanitized in accordance with preferred aspects of the present invention or the garments may be prepared by being hung on hangers or folded. The use of new hangers may be preferable over recycled hangers to reduce the risk of contaminant introduction. Where the garments are to be packaged in a container, such as a sling similar to sling 100 described above, the garments may first be packaged in a plastic wrap or the like to reduce the risk of contamination. Any such container may include features and/or be constructed of materials that are contamination resistant for delivery of the garments to the customer. Whether the garments are provided on hangers, folded, or simply packed and wrapped, it is preferable to pack the bundles of garments within a container for delivery to the customer. Preferably, a sling is utilized, which sling may be wholly or partially lined by an insertable liner material, such as plastic film or the like, and the slings themselves may be sanitized by an appropriate cleaning procedure. Like the slings 100 described above, dedicated slings can be utilized for a customer, which slings may be color-coded, marked or provide with indicia for that purpose. For hanging clothes, other appropriate containers are contemplated including features for hanging garments within containers and permit shipping thereof back to the customer facility. Also preferably, in the same manner as described above, tamper evident features may be incorporated into the packaging and/or container closures. Fully prepared garments are then preferably put into a clean storage station as indicated at 44 for a subsequent delivery step 46 of clean garments in accordance with desired standards back to the customer.

For any part or all of the processing after the laundering steps, mechanized systems may be used for transporting garments from station to station or garments can be transported manually. Automatic systems are known that move garments, such as provided on hangers from station to station and for tracking each garment, such as with a bar code or the like. Also, certain processing stations can be integrated into such an automated system, such as for moving garments at a controlled timing, temperature and environmental controls through a steam tunnel. Steam tunnels themselves are known; however, for purposes of the present invention it is further contemplated that by controlling the environment and temperature within a steam tunnel so as to achieve a garment temperature of around 290 degrees Fahrenheit or more within the tunnel, microbes can be further inhibited or killed.

Before the packed garments are stored at station 44, at least one garment from each lot is to be biologically inspected in accordance with an aspect of the present invention. Any number or all of the laundered garments can be biologically inspected in accordance with the present invention; however, it is preferred to sample the garments at an acceptable level and frequency to satisfy the garment services provider and its customer(s) of control of the garment process and compliance with any desired standard. Therefore, a sampling and testing step 48 is shown between the preparation step 42 and the storage step 44. It is preferable that a garment for sampling be taken after the garment inspection step 28 at any time, but it is only necessary that the garment be selected at any time after the launder process comprising the wash step 24 and dry step 26. A decision step is shown at 50 as to whether a garment passes the biological test admitted in step 48 or not to be used preferably as an indication of all garments of a particular lot of garments. Illustrated box 52 indicates a step further processing of the garments of a lot after a biological inspection and a failure of such inspection. Step 52 can comprise many different things, such as may be determined in accordance with customer needs or agreed upon protocols. As examples, one or more other garments of the lot can be tested by the biological inspection procedure to determine whether the lot should be acceptable for delivery or not. Or, the garments of a lot can be re-laundered. Alternatively, another further test may be done to the failed garment that is more specific to a particularly concerned biological contaminant. Depending on the level of the failure, different further steps may be conducted including the possibility of acceptance without further testing. Details of the garment biological inspection process are described in greater detail below.

The facility sanitization and biological inspection step 30 is illustrated after the laundering steps and before the inspection step 28. However, a facility sanitization and/or biological inspection can be done on any or all surfaces onto which the garments may come into contact after laundering at any time. The facility sanitization and biological inspection step 30 is illustrated before the inspection step 28 because it is preferable to conduct the inspection step 28 on a large surface suitable for spreading out a number of garments and looking them over as described above. Such a surface can be conventionally provided as a suitably sized table top that may be slanted to facilitate garment inspection, and may be comprised of conventional material, such as a commercial grade stainless steel that itself can be suitable for clean applications like food processing. Thus, the surface of such an inspection table is a preferable surface to sanitize and inspect for biological contaminants as a way to reduce the possibility of introducing biological contaminants to the garments during processing and as an indication of the cleanliness of the surface or the need to further clean such surface prior to garment contact. Step 30 represents both the steps of sanitizing and biologically inspecting a processing surface with the understanding that each procedure is actually an independent step and that either one or both procedures can be independently conducted in accordance with the present invention. Sanitization is a cleaning procedure as conducted to a processing surface that is specifically directed to the reduction and substantial elimination of any particular bacteria or other microbe or to any such class or group of microbes. Sanitization is understood to be obtained by the use or application of a specifically designed (and as are customarily registered with government agencies such as the Environmental Protection Agency in the United States) sanitizer comprising a chemical composition that is directed to killing any one or more of certain bacteria or other microbes. Multiple different sanitizers can be used together. The level of cleanliness or sanitization of any processing surface to be achieved in accordance with the present invention is the level that achieves what ever desired garment sanitization is required for any given bacteria or other microbe under the standards set or agreed by such a garment services provider and its customers and as may be based upon the garment use industry. For the food industry, substantial elimination of certain food bacteria from garments may be most important, and to do so, a substantial elimination of such bacteria from processing surfaces may be required. In a situation where a sanitizer is established as effective as applied to a facility processing surface to achieve a desired level of sanitization for a given garment application, a biological inspection procedure may be deemed unnecessary. A biological inspection procedure would still show compliance with desired cleaning protocols, if desired. On the other hand, where sanitary conditions exist for other reasons (i.e. the processing surface does not need to be further sanitized), biological inspection of the processing surface can be conducted to check that proper sanitary conditions are present and/or as a way of showing compliance with desired conditions or standards of garment sanitization.

Preferably also, records of the results of such facility biological inspection can be logged and provided to the customer to show compliance of the garment processing with the facility biological inspection procedures. Other surfaces that may be sanitized and/or biologically inspected include as examples folding station or packaging station surfaces or the like. Likewise, it is also contemplated that such facility sanitization and biological inspection steps can be conducted on packaging materials and/or containers if desired. Details of facility biological inspection processes are described in greater detail below.

As above, the facility biological inspection procedure is conducted not only to ensure that garments are processed (i.e. folded, sorted, and the like) on a clean surface so as not to add microbes to the garments, but also to establish and report to customers a consistent and clean processing environment. Again, any number of such facility surfaces can be inspected and any type of biological inspection test can be specifically conducted as are presently known or later developed based upon the inspection for one or more particular microbes, such as bacteria, as may be present on such surface(s). For purposes of describing a specific example, a preferable station set up and facility biological inspection procedure follows as the station comprises a product inspection station as is usable in step 28 described above.

A product inspection station preferably comprises a large surface onto which laundered garments can be provided such as comprised of commercially available stainless steel that is suitable for food processing applications. Such a surface is preferably provided where one or more workers can be located so as to stand and perform the inspection of the garments. The use of chairs or other items is contemplated, but not preferable, to limit the number of items that may provide contamination to the process. Preferably also, the workers are positioned to stand on an antimicrobial mat as are commercially available. Also, dirt tack mats are preferably provided for the workers to step on before they step on the antimicrobial mat to remove dirt particles from their shoes. The workers also preferably wear gloves, hairnets and special uniforms that are cleaned to be sanitized at least as well as the processed garments according to the present invention. Then, if the garments are directly loaded back into a sling, the sling is preferably processed in a similar manner for cleanliness and preferably includes top flaps to close the sling. Whereas such slings are typically also provided with flaps to close off the bottoms, it is preferable to provide a bottom liner that may also be sewn into the slings to minimize the possibility of contamination from below. Such slings may be supported on movable carts so that the inspected garments can be easily moved to a next station. To further minimize the possibility of contamination from below, it has been developed to design such carts to be easily cleanable and to design support element surfaces so as to exhibit easily cleanable flat surfaces without structures to catch dirt or other contaminants toward the sling.

Facilities Biological Inspection Procedures

A biological inspection test for the work surface is preferably conducted to a surface area of the work surface to make sure it is substantially free of microbes, such as bacteria. Preferably, the test is conducted before and after a sanitization step is conducted on the work surface for recording and to show compliance with desired clean protocols. Using a specific microbe test procedure, a suitable surface cleanliness or sanitization can be determined by tracking the microbe test results and empirically determining a suitable level of sanitization based upon the obtaining of desired threshold levels of microbe presence on the garments, as are preferably tested in a manner described below. Environmental testing of one or more facility surfaces also serves to establish a clean processing environment and to show the effectiveness of sanitizing techniques and products. Consistent testing over time shows the compliance with clean environmental standards as may be developed for a particular garment processing application and can be used to validate such environmental standard compliance. Preferably, the test method used is repeatable and consistently accurate regardless of the technician performing the procedure.

A preferred microbe test for a facility biological inspection procedure comprises an ATP test as such tests themselves have been developed for measuring an enzyme found in microorganisms to thus provide an indication of the level of bacteria or other microbial organisms that may be present on the surface. ATP, which stands for adinosine triphosphate, is a high-energy storage molecule that is made up of adinosine and other phosphate groups that serve as an energy source for all living cells. Specifically, when the ATP breaks down into adinosine diphosphate and phosphate, it releases energy used to fuel biochemical processes of microorganisms. In any case, an inspection process looking for ATP provides an established method of determining the presence of microbial organisms, such as bacteria and other microbes. A preferable ATP test can be conducted with ATP test devices and an ATP test reader that are commercially available from Charm Sciences Inc. of Lawrence Mass. Moreover, such devices and readers are the subject of U.S. Pat. Nos. 5,917,592, 6,055,050 and D393,601, the entire disclosures of which are hereby incorporated by reference. A preferable ATP reader is a reader commercially available from Charm Sciences Inc. under the trade name "LUM Giene." The ATP test elements preferably comprises those commercially available also from Charm Sciences Inc. that include a tube with chemical and a swab so that a surface can be swabbed, the swab can then be inserted within the tube and subsequently mixed with the chemical. Then, the ATP reader can determine an ATP count value to be recorded and empirically correlated with other readings before and after as a way of validating and/or establishing a clean processing environment and compliance. If desirable to check the effectiveness of a sanitization process, such as of a processing surface or the like, it is contemplated to first test a desired surface for ATP, then to clean the surface with a sanitizer or by a sanitization process, such as using an antimicrobial cleaner, as are commercially available, for example from the Ecolab Company in St. Paul, Minn., and then to retest the surface for ATP after the sanitization process. Such readings can be compared with other sanitizing processes, cleaners, or the like, or may be compared with developed standards obtained in any way. Also, the results can be reviewed against product inspection results as described below to monitor the attainment of clean products, such as garments. If, for example, product testing is unsatisfactory, any number of processing surfaces can be tested to facilitate the determination of any problem areas where sanitizing may need to be improved.

Garment Biological Inspection Procedures

The garment biological inspection test can comprise any suitable biological test that determines the presence of any particular microbe, such as bacteria, as may be desirable based on a specific application and use of the tested garments. A preferred biological test for bacteria as usable for garments to be used in the food industry follows and includes a CFU (colony forming unit) tester as is commercially available from the Minnesota Mining and Manufacturing Company of St. Paul Minn. that is available under the trade name "3M Quick Swab" from the 3M Microbiology Products Division. Such a CFU tester comprises test devices including swabs for wet or dry swabbing a product or environmental surface, such as a garment surface, and provides a tube containing a reactive chemical liquid for mixing with the swabs after a product or other surface is swabbed. In particular, the swab is provided within the tube, but separated from a letheen buffer broth also provided within an openable compartment of the tube. The swab is initially removed from the tube, preferably near the product surface to be tested, and then used to swab a predetermined area of the product, such as a garment surface. Preferably, the area of the garment surface tested is consistent from one garment to another over time, although the particular surface portion of the garment tested can vary or be chosen randomly as part of the test procedure. Then, the swab is returned to the tube and preferably returned to a lab facility or designated area in the processing facility where the CFU count will be determined, as described further below. As soon as possible after swabbing a surface, the letheen broth is mixed by the swab. To do this, the tube is manipulated to break open the broth compartment (by bending and opening a snap valve) and to permit flow of the letheen broth about the swab. Using the swab, the broth is then mixed with the swab by pressing and twisting the swab against the tube wall as immersed within the broth. Once mixed and the swab has been removed from the broth, the solution is poured onto a biological growth medium.

Preferably, the biological growth medium comprises a film like product also commercially available from the Minnesota Mining and Manufacturing Company of St. Paul, Minn. under the trade name "3M Pitrifilm™" Plates. One specific growth plate that is commercially available comprises an aerobic count plate that is preferred for use in garment testing in accordance with the present invention for inspecting for aerobic microorganisms. For other applications or conditions where other microbe inspection is desired, other such plates are also commercially available including plates that inspect for the enumeration of coliforms (as rapid, high sensitivity, and regular versions) *E. coli*, yeast and mold, enterobacteriaceae, staphylococcus aureus (staph), and listeria. Such plates can be used as desired for any particular application and may be used in combination as may be desirable. Of these plates, the aerobic count, coliform count, and *E. coli*/coliform count plates can presently be read in a specific reader that is also commercially available from the Minnesota Mining and Manufacturing Company of St. Paul, Minn. under the trade name "Pitri Film Plate Reader" including in particular model number 6499. This plate reader receives the count plates after they have been incubated for a desired standard time, which incubation time is determined on a microorganism specific basis and is set out specifically within instructions provided for each test procedure with the "3M Pitrifilm™" Plates. After a proper incubation period, the plate can be inserted within the plate reader to automatically provide a count and a screen image of the plate with color markings of the colonies showing the presence of CFU's.

For garment testing, a preferred protocol includes removing a swab from the test device and swabbing an area of the garment of between approximately one square inch to approximately nine square inches, preferably an area of about four square inches.

It is further understood that any on of the above or suggested CFU test procedures utilizing any kind of specific biological growth medium could be utilized as the test of the facilities biological inspection procedure instead of or in addition to the ATP test described above. Likewise, the ATP test procedure could be used for the garment testing. Moreover, as other test devices and procedures are developed and are or become commercially available, they may be substituted for one or both of the facilities and garment biological inspection procedures described throughout this application. Any such test procedure and test device may be chosen based upon the service field of the garments and a desire to inspect, monitor and/or minimize or maintain any particular microbe level below some threshold. Such a selected test procedure and device should be capable of providing results commensurate with the desired threshold measurement.

The invention claimed is:

1. A method of processing garments as used by a customer within a service field by a garment service provider at a garment service facility, the method comprising:
   performing a biological inspection both on a garment service facility surface and on a garment processed thereon; and
   comparing results from the garment biological inspection against results of the facility surface biological inspection to determine compliance with garment service facility biological inspection procedures.

2. A method of processing garments as used by a customer within a particular service field by a garment service provider at a garment service facility including the steps of:
   obtaining soiled garments from the customer;
   laundering the soiled garments by the steps of washing the garments and drying the garments;
   preparing the garments for delivery back to the customer;
   sanitizing a processing surface within the garment service facility, wherein the processing surface comprises a surface that is used in processing the garments after laundering;
   obtaining a biological sample from the processing surface and testing the sample for the presence of microbes to a level that is based upon the particular service field of the customer;
   obtaining a biological sample from at least one garment that has been laundered within the garment service facility and testing the sample for the presence of microbes to a level that is based upon the particular service field of the customer; and
   comparing garment biological sample results against processing surface sample results to determine compliance with garment service facility biological inspection procedures for the particular service field of the customer.

3. The method of claim 2, further comprising a step of conducting a facility biological inspection procedure on the processing surface within the garment service facility after the processing surface has been sanitized, wherein the biological inspection procedure comprises obtaining a biological sample from the surface used in processing garments and testing the sample for the presence of microbes.

4. The method of claim 3, wherein the facility biological inspection procedure is conducted on a surface of an inspection station after the laundering step and prior to any garments being processed thereon.

5. The method of claim 2, wherein the facility biological inspection procedure includes an ATP test.

6. The method of claim 2, wherein the garment biological inspection procedure includes a CFU test.

7. A method of processing garments as used by a customer within a service field by a garment service provider at a garment service facility including the steps of:
   obtaining soiled garments from the customer;
   laundering the soiled garments by the steps of washing the garments and drying the garments;
   preparing the garments for delivery back to the customer; and
   conducting a garment biological inspection procedure on at least one garment that has been laundered within the garment service facility while within the garment service facility by obtaining a biological sample from the garment and testing the sample for the presence of microbes;
   obtaining a biological sample from a processing surface and testing the sample for the presence of microbes; and
   comparing garment biological sample results against processing surface sample results to determine compliance with garment service facility biological inspection procedures.

8. The method of claim 7, further comprising a step of sanitizing a processing surface within the garment service facility, wherein the processing surface comprises a surface that is used in processing the garments after laundering.

9. The method of claim 8, further comprising a step of conducting a facility biological inspection procedure on the processing surface within the garment service facility, wherein the processing surface comprises a surface that is used in processing the garments after laundering and the biological inspection procedure comprises obtaining a biological sample from the surface used in processing garments and testing the sample for the presence of microbes.

10. The method of claim 9, wherein the facility biological inspection procedure is conducted on a surface of an inspection station after the laundering step and prior to any garments being processed thereon.

11. The method of claim 9, wherein the facility biological inspection procedure includes an ATP test.

12. The method of claim 9, wherein the garment biological inspection procedure includes a CFU test.

13. A method of processing garments as used by a customer within a service field by a garment service provider at a garment service facility by obtaining soiled garments from the customer, laundering the soiled garments by the steps of washing the garments and drying the garments, performing a biological inspection on both a facility surface and a garment processed thereon, comparing garment biological inspection results against processing surface inspection results to determine compliance with garment service facility biological inspection procedures, preparing the garments for delivery back to the customer, and controlling the handling of the garments between the garment service facility and the customer by transporting the garments within a container, wherein the container is provided with an indication that the garments are specified for a specific garment process that includes a biological inspection.

14. The method of claim 13, wherein the container comprises a sling.

15. The method of claim 14, wherein the sling includes at least one of a color-coding, specific indicia, marking, and a closure with a tamper evident feature.

16. The method of claim 14, further comprising a step of sanitizing a processing surface and conducting a facility biological inspection procedure on the processing surface within the garment service facility, wherein the processing surface comprises a surface that is used in processing the garments after laundering and the biological inspection procedure comprises obtaining a biological sample from the surface used in processing garments and testing the sample for the presence of microbes.

17. The method of claim 16, further comprising a step of conducting a garment biological inspection procedure on at least one garment while within the garment service facility by obtaining a biological sample from the garment and testing the sample for the presence of microbes.

18. The method of claim 17, wherein the facility biological inspection procedure includes an ATP test.

19. The method of claim 17, wherein the garment biological inspection procedure includes a CFU test.

20. A method of processing garments as used by a customer within a particular service field by a garment service provider at a garment service facility, the method including:
    sanitizing a processing surface within the garment service facility to a level that is based upon the particular service field of the customer;
    obtaining a biological sample from the processing surface and testing the sample for the presence of microbes to a level that is based upon the particular service field of the customer;
    obtaining a biological sample from a garment that has been laundered within the garment service facility while within the garment service facility and testing the sample for the presence of microbes to a level that is based upon the particular service field of the customer; and
    comparing garment biological sample results against processing surface sample results to determine compliance with garment service facility biological inspection procedures for the particular service field of the customer.

21. The method of claim 20, wherein the method includes reporting garment biological sample results and processing surface sample results to the customer, including comparison thereof.

* * * * *